(12) United States Patent
Beebe

(10) Patent No.: US 6,676,642 B2
(45) Date of Patent: Jan. 13, 2004

(54) BARREL STABILIZER FOR SYRINGE PISTON

(75) Inventor: W. Scott Beebe, Ashland, MA (US)

(73) Assignee: Fishman Corporation, Hopkingon, MA (US)

( * ) Notice: Subject to any disclaimer, the term of this patent is extended or adjusted under 35 U.S.C. 154(b) by 61 days.

(21) Appl. No.: 09/902,379

(22) Filed: Jul. 10, 2001

(65) Prior Publication Data

US 2002/0016572 A1 Feb. 7, 2002

Related U.S. Application Data

(60) Provisional application No. 60/216,943, filed on Jul. 10, 2000.

(51) Int. Cl.[7] .............................................. A61M 5/315
(52) U.S. Cl. ...................................................... 604/228
(58) Field of Search ................................ 604/228, 229, 604/230, 235, 218–221, 222, 225, 187

(56) References Cited

U.S. PATENT DOCUMENTS 4,159,713 A * 7/1979 Prais ........................... 128/765
4,906,231 A * 3/1990 Young ......................... 604/110
6,042,565 A * 3/2000 Hirschman et al. ......... 604/155

\* cited by examiner

Primary Examiner—Brian L. Casler
Assistant Examiner—Ann Y Lam
(74) Attorney, Agent, or Firm—Cesari and McKenna, LLP; Edwin H. Paul, Esq.

(57) ABSTRACT

A stabilizer for a piston that strengthens the piston when higher dispensing volumes and/or pressures are involved. The stabilizer intimately contacts the piston along the radius of the piston to prevent distortion of the piston thereby preventing the fluid being dispensed from flowing around the piston destroying repeatability, accuracy and contaminating the driving mechanisms. The stabilizer also prevents the piston from cocking that may make the dispensing inaccurate and non-repeatable. The stabilizer may be of substantially any material from metals to any of the plastics suitable for maintaining its structural integrity under the pressures and forces involved.

8 Claims, 2 Drawing Sheets

BARREL STABILIZER FOR SYRINGE PISTON

CROSS-REFERENCE TO RELATED APPLICATIONS

The present application claims priority from U.S. Provisional Patent Application Ser. No. 60/216,943, which was filed on Jul. 10, 2000, by W. Scott Beebe for a "Barrel Stabilizer for Syringe Piston" and which provisional is hereby incorporated herein by reference.

BACKGROUND OF THE INVENTION

1. Field of the Invention

This invention relates generally to pistons and syringes, and, more particularly to industrial pistons and syringes and even more particularly to such pistons and syringes made of pliable materials, for example plastics.

2. Background Information

Plastic syringes have been finding increasing use in industrial applications requiring precise dispensing of a wide variety of fluids. Plastic syringes are finding favor since they are disposable and relatively inert to many solvents and other material being dispensed. Moreover, the pliable plastic pistons allow the release of air trapped in the syringe barrel, prior to dispensing, around the piston itself prior to and during the dispensing of fluids. The air free syringe combined the technology of the dispensing apparatus provide accurate and repeatable dispensing volumes. The materials being dispensed may have a wide range of viscosities from very viscous, like epoxies, to water.

Typically the syringe is filled with a viscous fluid that traps air near the piston. With viscous fluids the approach of tipping the syringe needle point outlet up to allow the air to rise is not efficient because it takes too long. The more typical approach is to manually drive the piston as if to dispense the fluid but to do so that the pressure and the pliable piston and syringe body allow the trapped air to escape around the piston.

However, it is the pliable plastic materials that provide the advantage of allowing air to bypass the piston present some limitations that are proving troublesome in practice. One such problem occurs when larger diameter pistons are used and/or high pressures occur in the barrel of the syringe. In such cases the fluid tends to bypass or "blow by" the piston. "Blow by" refers to the material meant to be dispensed traveling around the piston (as the air did as described above) thereby infiltrating and eventually destroying repeatability and accuracy of the dispensed volume. When dispensing fluid by driving the fluid out the needle output, the pressure acts in all directions including trying to drive the fluid around the piston where the piston and the syringe body intersect. High enough pressure will overcome the pliable material resistance and will force the fluid around the piston causing the blow by problem. The blow by problem occurs in virtually in all syringes, but it occurs more often and is more of a problem in higher volume dispensing systems using large diameter syringes. In particular industrial syringes in the 30 cc range and higher are especially susceptible to such problems and limitations because the piston diameters become large and the pressures and forces at the outer ends of the pistons where the piston meets the inner surface of the syringe body become large enough to distort the piston and or the syringe body. The large diameter syringe piston has a longer "moment arm" (the radius). It becomes easier to distort the piston by at the far edge due to the mechanical advantage of the longer moment arm. The pressure loss in the syringe combined with fluid exiting past the piston as opposed to out the needle point outlet destroys the systems accuracy and repeatability. Furthermore, it may damage the fluid dispensing equipment. Such fouling requires that the equipment be disassembled and cleaned or discarded.

Another limitation of known syringe dispensing systems occurs when the piston becomes cocked in the barrel of the syringe. When this happens the syringe may continue to function, but the dispensing amounts will be inaccurate and non-repeatable.

Another limitation of known syringe dispensing systems occurs when the piston is held stationary by a mechanical arm during dispensing creating pressure in the syringe chamber. Said pressure causes the outside edges of the plastic piston to deflect. This deflection will destroy accuracy and repeatability of dispensing outputs.

It is an object of the present invention to prevent cocking of the piston and "blow by" by providing a strengthening and stabilizing support that substantially prevents "deflection of the piston" in industrial syringes.

SUMMARY OF THE INVENTION

The object set forth above as well as further and other objects and advantages of the present invention are achieved by the embodiments of the invention-described hereinbelow.

The barrel stabilizer is an insert that mates with the piston in an industrial syringe. The piston is attached to the mechanized drive via a threaded engagement housed by the stabilizer. The stabilizer extends across the diameter of the piston thereby strengthening the piston to sustain higher pressures and dispensing quantities and increases the overall height to eliminate any possibility of the piston cocking inside the syringe.

The stabilizer is arranged to mount into the piston on the side not facing the fluid, in a preferred embodiment, after any trapped air has been eliminated. In a preferred embodiment the stabilizer is arranged as a split barrel that is assembled like a claim shell embracing the drive rod and supporting the piston. The two halves of the barrel may be joined by screws, belts or springs wrapped around the barrel, adhesives or other known techniques.

The stabilizer can be made from metal, wood, plastic or virtually any solid material that provides mechanical integrity for the pressures and forces involved. In a preferred embodiment, plastic is used.

For a better understanding of the present invention, together with other and further objects thereof, reference is made to the accompanying drawings and detailed description and its scope will be pointed out in the appended claims

BRIEF DESCRIPTION OF THE DRAWINGS

The invention description below refers to the accompanying drawings, of which.

DETAILED DESCRIPTION OF AN ILLUSTRATIVE EMBODIMENT

Figure 1A:
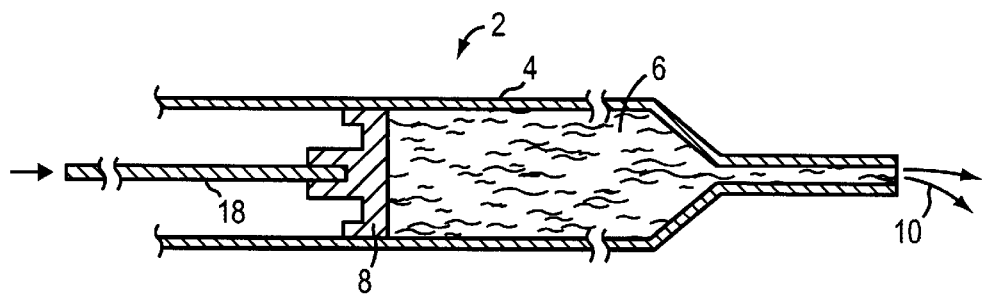
FIG. 1A is a prior art drawing demonstrating a problem.
Figure 1B:
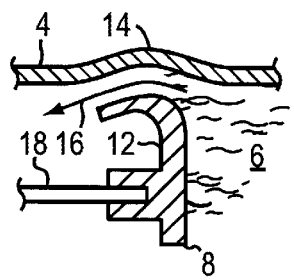
FIG. 1B is a detail of FIG. 1A showing a problem.

A known industrial syringe 2 is shown in FIG. 1A with hollow body 4 filled with a liquid 6 before the piston 8. The piston moves compressing the liquid and drives the liquid out the exit port 10. In FIG. 1B, one limitation of the syringe is demonstrated. When the pressure created by compressing the liquid in hollow body 4 becomes greater than the sealing capacity of the piston 8 and/or the wall strength of hollow body 4 and/or the rigidity of the plastic used, the piston will distort 12. Also the body of the hollow syringe may distort 14. In either case the fluid 6 will be able to by pass the piston 16 and flow into the drive rod 18 cavity. Continued blow by will result in destroying accuracy and repeatability of the output of exit port 10. Futhermore, fouling of the drive mechanism and require flushing and cleaning of the fluid that by passed the piston.

Figure 2:
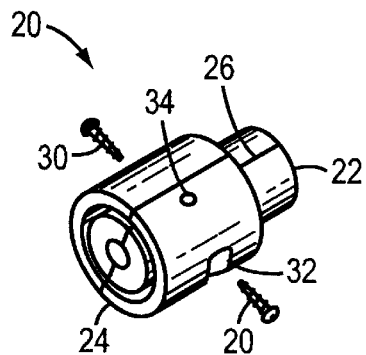
FIG. 2 is an isometric projection drawing of the stabilizer.
Figure 3:
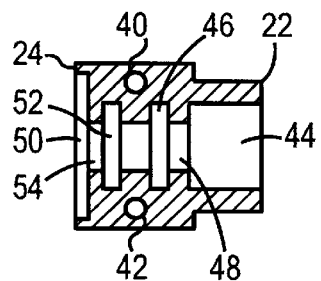
FIG. 3 is a cross section of the stabilizer.

FIG. 2 show a projection drawing of a clam shall, split barrel stabilizer 20 built in accordance with the present invention, and FIG. 3 is a cross section of the stabilizer. The stabilizer may be made of metal, for example aluminum, but low-density polyethylene and other such material may also be used in preferred embodiments. The width of the end 22 of the stabilizer may be made to fit with a piston on any size syringe. The other end 24 is made to fit with the drive rod. The fittings at both ends are typically a clam shell split 26 barrel that embraces the syringe piston and the drive rod. The two halves are joined by screws 28 and 30. The slot 32 receives the head of screw 28 and the hole 34 extends from the opposite slot (not shown) where the screw 30 is used. The two screws insert from opposite sides of the stabilizer. Other attachment means may be used. For example, the attachment mechanisms may be, but not limited to, a threaded or tapped fit, a friction fit, a bayonet type fit, a snap-in fit, arrangements using set screws, and similar known mechanisms and combinations thereof.

FIG. 3 shows one half of the stabilizer. The holes 40 and 42 are extensions from the hole 34 and the hole that extends from the slot 32. The stabilizer at end 22 has a circular hollow 44 that is meant to receive a mating extension from a syringe piston. The syringe piston extension is configured to be retained by the circular cutout 46 connected to the syringe piston by a smaller diameter neck 48. The drive rod 18 is arranged with a terminus similar in design to the end of the syringe piston. There is a circular hollow 50 and a circular cutout 52 joined to the hollow by a smaller neck 54.

Figure 4:
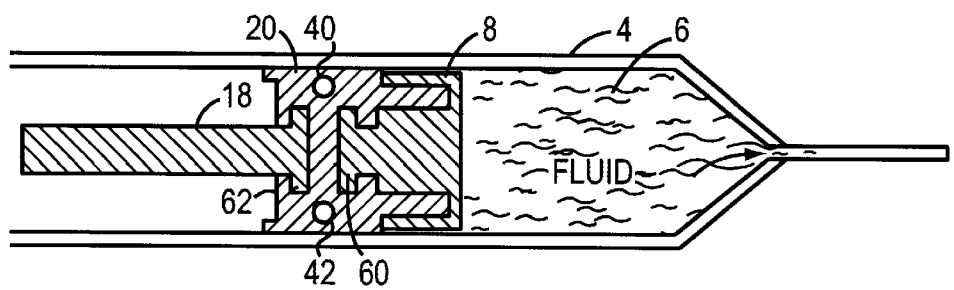
FIG. 4 is a drawing of the stabilizer/drive rod/syringe body in place.

FIG. 4 shows an assembly of the syringe 4, syringe piston 8, barrel stabilizer 20 and drive rod 18 in cross section. Notice how the extension from the syringe piston 60 is retained in the circular cutout 46 and similarly how the extension from the end 62 of the drive rod is retained in the cutout 52. Other arrangements can be used to accomplish syringe piston stabilization.

Figure 5:
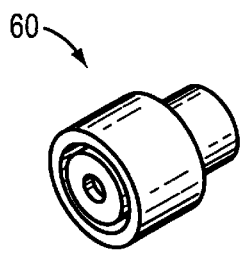
FIG. 5 is an isometric of another preferred embodiment.
Figure 6:
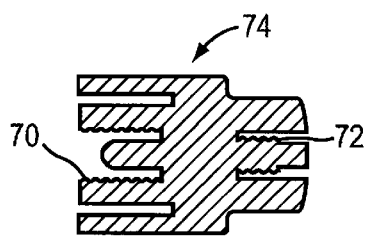
FIG. 6 is a cross section of the embodiment in FIG. 5.

FIG. 5 shows another embodiment of the barrel stabilizer 60 with similar external dimensions to stabilizer 20, however, with threaded connections. FIG. 6 shows the stabilizer in cross section. There is an inner tapped thread 70 that mates with the outer threaded portion of the drive rod and an outer thread 72 that mates with an inner threaded piston. The direction (left or right hand) of these threads is selected to reduce loosening by arrangement so that when the syringe is dispensing fluid the drive mechanisms tend to work to tighten the threaded connections. The pitch of the threaded connections are selected from those typically used for the materials. When the stabilizer is attached to the piston the combination provides a stronger structure that better withstands the pressures and forces involved so that the combination will support higher pressures and forces without distorting and thus without allowing fluid to by pass the structure. If the stabilizer is made of metal the pressure can exceed several hundred psi and dispensers delivering more than several ml per minute can be accommodated with minimal fluid by passing the piston. If the stabilizer is made from polyethylene the thickness of the stabilizer 74 can be made to accommodate pressures and deliver amounts comparable to the use of a metal to stabilizer. In practice the dimensions and therefor the strength of the stabilizer and the piston stabilizer combination can be made to accommodate the entire range of pressures and dispensing volumes used in the art.

Figure 7:
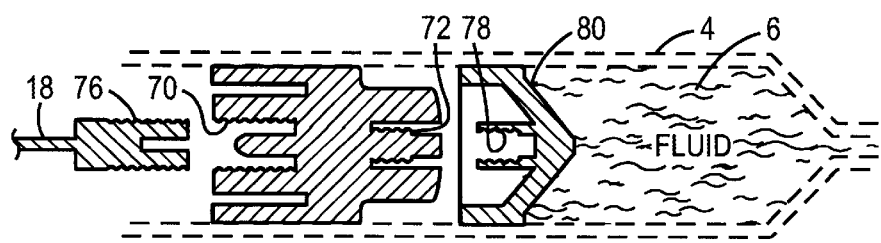
FIG. 7 is a combination of mating parts of a preferred embodiment in cross section.

FIG. 7 shows the combination of the threaded stabilizer and the piston and drive rod combination. The outer thread 76 of the drive rod 18 is mated with the stabilizer tapped portion 70. The threaded portion 72 of the stabilizer is, in turn, mated with the tapped portion 78 of the piston 80. The attachments can be made in any order. The body 4 of the syringe is shown with fluid 6 for dispensing for clarity.

Although the invention has been described with respect to various embodiments, it should be realized this invention is also capable of a wide variety of further and other embodiments within the spirit and scope of the appended claims.

What is claimed is:

1. A stabilizer for a piston within a hollow syringe housing comprising:
    a barrel defining a body with first end suitable for connecting to an adjoining surface of the piston and a second end suitable for connecting to a drive rod,
    a first threaded connection connecting the first end to the piston,
    a second threaded connection connecting the second end to the drive rod, and
    an extension from the body extending along and interferingly contacting the adjoining piston surface in order to maintain the piston against the inner surface of the hollow syringe housing, and wherein the extension from the body continues to extend along the adjoining piston surface until the extension reaches the inner surface of the hollow syringe housing.

2. The stabilizer as defined in claim 1 wherein the first and second means for connecting comprise threaded connections.

3. The stabilizer as defined in claim 1 wherein the stabilizer is constructed from metal.

4. The stabilizer as defined in claim 1 wherein the stabilizer is constructed from a plastic material.

5. A stabilizer for a piston within a hollow syringe housing comprising:
    a barrel defining a body with first end suitable for connecting to an adjoining surface of the piston and a second end suitable for connecting to a drive rod,
    a first threaded connection connecting the first end to the piston,
    a second threaded connection connecting the second end to the drive rod,
    an extension from the body extending along and interferingly contacting the adjoining piston surface and extending to the inner surface of the syringe, and the extension extending farther along and adjacent to the inner surface of the syringe such that the stabilizer/piston combination remains straight and aligned with the syringe body when the piston exerts pressure on a fluid being dispensed.

6. The stabilizer as defined in claim 5 further wherein the stabilizer is split longitudinally into two substantially equal portions, and further comprising means for joining the two portions together.

7. A method for stabilizing a piston within a hollow syringe housing comprising the steps of:

defining a barrel body with first end suitable for connecting to an adjoining surface of the piston and a second end suitable for connecting to a drive rod, threading the first end into a corresponding threaded portion of the piston, threading the second end into a corresponding threaded portion of the drive rod, and extending the body along and interferingly contacting the adjoining piston surface in order to maintain the piston against the inner surface of the hollow syringe housing, and further extending the body along and adjacent to the inner surface of the syringe such that the stabilizer/piston combination remains straight and aligned with the syringe body.

8. The method as defined in claim 7 further wherein the stabilizer is split longitudinally into two substantially equal portions, and further comprising the step of joining the two portions together.

* * * * *